(12) United States Patent
Vitari et al.

(10) Patent No.: US 10,633,649 B1
(45) Date of Patent: Apr. 28, 2020

(54) METHODS FOR PROFILING EXTRACELLULAR VESICLES FROM COMBINATORIAL PHAGE DISPLAY LIBRARIES

(71) Applicant: Verily Life Sciences LLC, Mountain View, CA (US)

(72) Inventors: Alberto Clemente Vitari, Mountain View, CA (US); Joshua Simon Klein, Mountain View, CA (US); Nathan Higginson-Scott, Mountain View, CA (US); Nathan Pierce, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 183 days.

(21) Appl. No.: 15/493,615

(22) Filed: Apr. 21, 2017

Related U.S. Application Data

(60) Provisional application No. 62/326,467, filed on Apr. 22, 2016.

(51) Int. Cl.
    *C40B 30/04* (2006.01)
    *C12N 15/10* (2006.01)

(52) U.S. Cl.
    CPC .......... *C12N 15/1037* (2013.01); *C40B 30/04* (2013.01)

(58) Field of Classification Search
None
See application file for complete search history.

(56) References Cited

PUBLICATIONS

Molek et al. (Jan. 21, 2011) Molecules vol. 16 pp. 857 to 887.*
Pruszynski et al., "Targeting Breast Carcinoma with Radioiodinated Anti-HER2 Nanobody," Nucl Med Biol, Author manuscript; available in PMC Jan. 1, 2014, pp. 1-20.
Bazan, Justyna, et al., "Phage Display—A Powerful Technique for Immunotherapy", Human Vaccines & Immunotherapeutics, 2012, vol. 8(12), pp. 1829-1835, doi:10.4161/hv.21704.

(Continued)

*Primary Examiner* — Christian C Boesen
(74) *Attorney, Agent, or Firm* — McDonnell Boehnen Hulbert & Berghoff LLP

(57) ABSTRACT

A method for profiling extracellular vesicles (EV) is provided. The method includes: (a) incubating isolated EV from one or more sources with a phage display library under conditions suitable for forming EV-bound phage, wherein the phage display library comprises one or more types of phage, each type of phage having a displayed proteinaceous display binding moieties capable of recognizing one or more epitopes on the surface of the EV, wherein each type of phage comprises nucleic acids encoding the displayed proteinaceous display binding moieties, and wherein the displayed proteinaceous display binding moieties of each type of phage is different; (b) isolating the EV-bound phage; (c) extracting the nucleic acids from the EV-bound phage; (d) amplifying the extracted nucleic acids; (e) sequencing the amplified nucleic acids to identify specific nucleic acid sequences associated with each type of phage from the library that are enriched from the isolated EV; and (f) comparing the specific nucleic acid sequences (output) with nucleic acid sequences from the phage display library (input) and nucleic acid sequences from a control to identify sequences that can distinguish between EV from the one or more sources.

7 Claims, 2 Drawing Sheets

Specification includes a Sequence Listing.

(56) References Cited

PUBLICATIONS

Carvalho, Joana, et al., "Extracellular Vesicles—Powerful Markers of Cancer Evolution", Front. Immunol., Jan. 12, 2015, pp. 1-7, http://journal.frontiersin.org/article/10.3389/fimmu.2014.00685/full.
De Laat, PPM., "Extracellular Vesicles in Circulation", Thesis, 2012, Pim de Laat, pp. 1-10, https://dspace.library.uu.nl/bitstream/handle/1874/thesis.
DePalma, Angelo, "Protein Profiling Poised to Make its Mark—Understanding Which Proteins are Expressed Under Which Circumstances", Genetic Engineering & Biotechnology News, Jan. 1, 2006, vol. 26(1), pp. 1-6.
De Toro, Julieta, et al., "Emerging Roles of Exosomes in Normal and Pathological Conditions: New Insights for Diagnosis and Therapeutic Applications", Frontiers in Immunology, May 4, 2015, vol. 6, Article 203, pp. 1-12, doi:10.3389/fimmu.2015.00203.
György, Bence, et al., "Therapeutic Applications of Extracellular Vesicles: Clinical Promise and Open Questions", Annu Rev Pharmacol Toxicol, 2015, vol. 55, pp. 439-464, doi:10.1146/annurev-pharmtox-010814-124630.
Julich, Henrike, et al., "Extracellular Vesicle Profiling and their Use as Potential Disease Specific Biomarker", Front Immunol., 2014, vol. 5, p. 413, doi:10.3389/fimmu.2014.00413.
Larman, H. Benjamin, et al., "Application of a Synthetic Human Proteome Discovery through PhIP-Seq", Nature Biotechnology, Jun. 2011, vol. 29(6), pp. 535-541, doi:10.1038/nbt.1856.
Larman, H. Benjamin, et al., "Autoantigen Discovery with a Synthetic Human Peptidome", Nature Biotechnology, Jun. 2011, vol. 29(6), pp. 535-543, doi:10.1038/nbt.1856.
Larman, H. Benjamin, et al., "PhIP-Seq Characterization of Autoantibodies from Patients with Multiple Sclerosis, Type 1 Diabetes and Rheumatoid Arthritis", Journal of Autoimmunity, 2013, vol. 43, pp. 1-9.
Larman, H. Benjamin, et al., "Cytosolic 5'-Nucleotidase 1A Autoimmunity in Sporadic Inclusion Body Myositis", Ann Neurol, Mar. 2013, vol. 73(3), pp. 408-418, doi:10.1002/ana.23840.
Lee, Carol, M.Y., et al., "Selection of Human Antibody Fragments by Phage Display", Nature Protocols, 2007, vol. 2(11), pp. 3001-3008, doi:10.1038/nprot.2007.448.
Loureiro, Liliana, et al., "Challenges in Antibody Development Against Tn and Sialyl-Tn Antigens", Biomolecules, 2015, vol. 5(3), pp. 1783-1809, doi:10.3390/biom5031783.
Marcus, Michelle, E., et al., "FedExosomes: Engineering Therapeutic Biological Nanoparticles that Truly Deliver", Pharmaceuticals (Basel), May 2013, vol. 6(5), pp. 659-680, doi:10.3390/ph6050659.
Siegel, Don, L., "Diagnostic and Therapeutic Applications of Phage Display Technology", Emerging Technologies in Transfusion Medicine, 2003, pp. 55-93.
Taylor, Douglas, D., et al., "Methods of Isolating Extracellular Vesicles Impact Down-Stream Analyses of their Cargoes", Methods, Oct. 1, 2015, vol. 87, pp. 3-10, doi:10.1016/ymeth.2015.02.019, Epub Mar. 10, 2015.
Xitong, Dang, et al., "Targeted Therapeutic Delivery Using Engineered Exosomes and its Applications in Cardiovascular Diseases", Gene, Jan. 10, 2016, vol. 575, (Part 2), pp. 377-384. (Abstract only).
Xu, George J., et al., "Viral Immunology. Comprehensive Serological Profiling of Human Populations Using a Synthetic Human Virome", Science, Jun. 5, 2015, vol. 348(6239), pp. aaa0698-1-aaa0698-9, doi:10.1126/science.aaa0698.
Yáñez-Mo, Maria, et al., "Biological Properties of Extracellular Vesicles and their Physiological Functions", Journal of Extracellular Vesicles, 2015, vol. 4, p. 27066, doi:10.3402/jev.v4.27066.
HuSdL™ Phage Display—Human Single Domain Antibody Library Kit, Creative™ BioLabs, 2011, pp. 1-12.
Premade Single Domain Antibody Library, Creative Labs. [Retrieved from the Internet Mar. 31, 2016: <URL:http://www.creative-biolabs.com/Premade-single-domain-antibody-library.html>].
Phage Display, pp. 1-9. [Retrieved from the Internet Apr. 1, 2016: <URL:https://en.wikipedia.org/wiki/Phage_display>].

\* cited by examiner

SEQUENCE LISTING

<160> NUMBER OF SEQ ID NOS: 4

<210> SEQ ID NO 1
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 1
aatgatacgg cgaccaccga gatctacacg ggggaggctt ggtacagcct            50

<210> SEQ ID NO 2
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 2
caagcagaag acggcatacg agatagacgg tgaccagggt tccctga              47

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
cactcattag gcaccccag                                              19

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonculeotide

<400> SEQUENCE: 4
gttatccgct cacaattcca c                                           21

METHODS FOR PROFILING EXTRACELLULAR VESICLES FROM COMBINATORIAL PHAGE DISPLAY LIBRARIES

CROSS-REFERENCE

This application claims the benefit of priority from U.S. provisional application Ser. No. 62/326,467, filed Apr. 22, 2016, which is incorporated by reference in its entirety.

BACKGROUND

Unless otherwise indicated herein, the materials described in this section are not prior art to the claims in this application and are not admitted to be prior art by inclusion in this section.

Extracellular vesicles (EVs) are membrane surrounded structures released by cells that have been recognized as potent vehicles of intercellular communication, both in prokaroytes and eukaryotes. This is due to their capacity to transfer proteins, lipids and nucleic acids, thereby influencing various physiological and pathological functions of both recipient and parent cells. In recent years, EVs have been intensely investigated as a novel and unique analyte to detect and differentiate among various chronic diseases and cancer as well as monitor their progression and possibly assess treatment outcome. However, only a very limited numbers of surface markers were explored in vivo on tumor derived EVs, making disease and cancer differentiation with EVs challenging. Accordingly, there is a need for a method for systematically characterizing EVs so that they can be used for such clinical and diagnostic applications.

SUMMARY

The present invention is directed to methods for profiling EVs from combinatorial phage display libraries.

In one aspect, a method for profiling extracellular vesicles (EV) is provided. The method includes: (a) separately incubating isolated EV from one or more sources with a phage display library under conditions suitable for forming EV-bound phage, wherein the phage display library comprises one or more types of phage, wherein each type of phage having a displayed proteinaceous display binding moieties capable of recognizing one or more epitopes on the surface of the EV, wherein each type of phage comprises nucleic acids encoding the displayed proteinaceous display binding moieties, and wherein the displayed proteinaceous display binding moieties of each type of phage are different; (b) isolating the EV-bound phage; (c) extracting the nucleic acids from the EV-bound phage; (d) amplifying the extracted nucleic acids; (e) sequencing the amplified nucleic acids to identify specific nucleic acid sequences associated with each type of phage from the library that are enriched from the isolated EV; and (f) comparing the specific nucleic acid sequences with nucleic acid sequences from the phage display library and nucleic acid sequences from a control library to identify sequences that can distinguish between EV from the one or more sources.

In one embodiment, proteinaceous display binding moieties comprise domain antibodies (DAB), single chain variable fragments, fragment antigen binding fragments (FAB), single chain variable fragments (scFv), affibodies, affimers, or peptides. In another embodiment, the isolated EVs are obtained from a bodily fluid. In certain embodiments, the isolated EV is obtained cell lines, serum, plasma, urine, saliva, or cerebral fluid. In another embodiment, the EV-bound phage complexes can be isolated by immunoprecipitation, polymer precipitation, ultracentrifugation, or affinity purification. In some embodiments, M13 phage is used to generate the phage display library.

DETAILED DESCRIPTION

Figure 1:
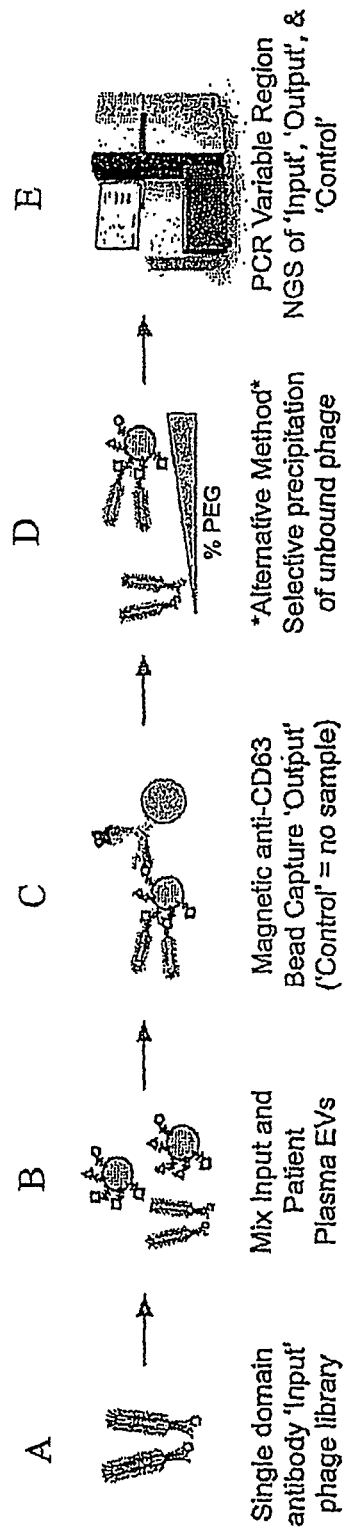
FIG. 1 is a general schematic showing the incubation of an "input" phage display library with isolated EVs from a source to form an "output" EV-bound phage complex. A "Control" sample formed by the incubation of an input phage display library without EVs is also generated. The variable regions of DNA extracted from the Input, Output and Control is then PCR amplified and subject to sequencing, e.g., NGS. To determine enriched sequences of the single domain antibodies.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Overview

Extracellular vesicles (EVs) are small circulating vesicles that can carry and transmit information from their cell of origin and can be isolated from a broad range of biological fluids by relatively non-invasive methods. EV-derived biomarkers have been proposed for a range of diseases including glioblastoma, pancreatic cancer, ovarian cancer, and acute myeloid leukemia. However, the number of validated surface biomarkers on EVs is limited. In addition, EVs are amenable to analysis by high throughput and high dimensionality analytical tools such, as but not limited, to mass-spectroscopy discovery-based proteomics. However, current methods are unable to measure the entire functional lipidome or proteome of EVs that include multiple isoforms, mutations, and post-translational modifications such as glycosylation and phosphorylation that have the potential to serve as molecular biomarkers of a patient's disease state. Thus, a method that has the potential to recognize molecular epitopes that have yet to be characterized and can be used to enable disease classification would be highly desirable.

Phage Immunoprecipitation Sequencing (PhIP-Seq) technology has demonstrated the power of combining phage display libraries with next generation sequencing (NGS) for profiling a patient's repertoire of circulating antibodies (Larman et al., 2011, Nature Biotech., Vol. 29(6), pp. 535-541; Larman et al., 2013, J. Autoimmun., Vol. 43, pp. 1-9; Larman et al., 2013, Ann. Neuro., Vol. 73, pp. 408-418; Xu et al., 2015, Science, Vol. 348(6239), pp. 1105, which are incorporated by reference in their entirety). In this approach, an 'Input' library of T7 phage displaying peptides is designed to cover sequences derived from a large collection of known proteins, for example all human open reading frames. An aliquot of this library is incubated with a patient sample known to contain antibodies, such as a serum. The antibodies are then immunoprecipitated using protein A/G coupled magnetic beads, bringing with them phage that are bound. These bound phage are the 'Output'. The 'Control' output phage are those that bind to the beads in the absence of patient samples. Extraction, PCR amplification, and next generation sequencing (NGS) of the phage's peptide sequence allows the calculation of an enrichment score for individual peptide sequences based upon the number of reads in the Input, Control, and Output. Although PhIP-Seq technology is highly multiplexed and sensitive, the technology is only capable of profiling a patient's antibody repertoire for binding to peptides with 100% homology to segments of known proteins and thus cannot be applied to studying EVs since they do not contain antibodies. In this disclosure, a method has been developed to explore unidentified molecular epitopes of EVs in an unbiased manner which in turn can be useful in identifying disease states.

As opposed to PhIP-Seq as well as VirScan (Xu et al., 2015, Science, Vol. 348(6239), pp. 1105), which starts with a defined library of peptide display elements with 100% sequence identity to segments of known human or viral proteins respectively, the method of the disclosure can start with a phage display library of any proteinaceous derived display elements such as but not limited to domain antibodies (Dab), single chain variable fragments (scFv), fragment antigen binding antibodies (Fab), affibodies, affimers, or peptides that are randomized within one or more complementarity determining regions and capable of recognizing a vast array of molecular epitopes present on the surface of EVs. An example of a starting "Input" phage display library can be, for example, an M13 phage single domain antibody (Dab) library with $10^9$ unique complementarity determining regions. The complementarity determining regions of the phage can be amplified by any suitable means, e.g., PCR, and sequenced, for example by NGS, to determine the variability in clone count of the Input library. Oligonucleotide sequencing or alternative methods like mass spectrometry could be used to characterize the library composition. The input library can then be incubated with EVs isolated by any suitable method from different sources. Phage bound specifically to EVs are then isolated to form an "Output" library. The 'Control' output phage are those phage that bind to the beads or are resistant to the precipitation condition in the absence of patient samples. The DNA of the isolated EV-bound phage can then be extracted, PCR amplified, and subjected to NGS to identify phage sequences that are enriched from each source of isolated EVs. The sequences of these unique 'Output' libraries of enriched phage will be compared to the 'Input' and 'Control' libraries to determine individual sequences that can distinguish between different sources of EVs. The cognate receptors of individual library elements can be identified using standard affinity pull downs coupled with mass spectrometry. Multiple sequential cycles of library enrichment could be performed to achieve the desired level of enrichment.

Extracellular Vesicles

Extracellular vesicles (EVs) are defined herein as membrane surrounded structures released by cells that have been recognized as potent vehicles of intercellular communication, both in prokaryotes and eukaryotes. EVs include exosomes and activation- or apoptosis-induced microparticles/microvesicles (MPs/MVs) and due to their capacity to transfer proteins, lipids and nucleic acids, they are able to influence various physiological and pathological functions of both recipient and parent cells. Body fluid-derived EVs are mixtures of vesicles that originate from different sources such as the cells found in body fluids and/or cells lining the cavities of extruded body fluids. The lipid membrane of EVs encapsulate and protects their contents from enzymatic attack and thus protects them as a source of physiological and pathological information. EVs from different sources including bodily fluids can be isolated by any suitable method such as but not limited to ultracentrifugation, precipitation, and/or affinity purification. Examples of sources of EVs may include: cell lines and bodily materials and fluids such as blood, serum, plasma, urine, saliva, cerebrospinal fluid, amniotic fluid, bile, breast milk, and feces. In some embodiments, sources of EVs can include cell lines isolated from different cancers, cell lines isolated from different healthy tissues, serum of subjects with different cancers, cerebrospinal fluid from patients with Multiple Sclerosis, serum or cerebrospinal fluid from healthy subjects, and serum of patients treated with different therapeutics. See, for instance, Yanez-Mo et al., 2015, J. Extracellular Vesicles, Vol. 4, pp. 27066, which are incorporated by reference in their entirety.

Phase Display Libraries

A "phage-display library" are defined herein as a protein expression library, constructed in bacteriophage, e.g., an M13-derived vector, that expresses a collection of cloned protein sequences as fusions with a phage coat protein. Thus, single-chain recombinant proteins having ligand-binding potential are expressed as fusion proteins on the exterior of the phage particle. This disposition advantageously allows contact and binding between the recombinant binding protein and an immobilized ligand such as a biomarker on a surface of EV. Those having ordinary skill in the art will recognize that phage clones expressing binding proteins specific for the ligand can be substantially enriched by serial rounds of phage binding to the immobilized ligand, dissociation from the immobilized ligand and amplification by growth in bacterial host cells.

In one embodiment, a phage display library includes any suitable proteinaceous derived display elements such as but not limited to domain antibodies (Dab), single chain variable fragments (scFv), fragment antigen binding antibodies (Fab), affibodies, affimers, or peptides that are randomized within one or more complementarity determining regions and capable of recognizing a vast array of molecular epitopes present on the surface of EVs is provided. An example of a starting library would be an M13 phage single domain antibody (Dab) library with $10^9$ unique hypervariable region elements. A phage display library displays a protein scaffold, e.g., immunoglobulin, with mutable solvent exposed hypervariable regions, on the surface of a biological carrier, e.g., phage, capable of propagation. The biological carrier includes a genetic expression cassette encoding the displayed protein thereby linking genotype with phenotype. This feature can allow for the construction of one-pot combinatorial libraries of over $1\times10^8$ variants, $1\times10^9$ variants or $1\times10^{10}$ variants. The most common type of display hosts are bacteriophages such as coli phage M13, fd filamentous phage, T4, T7, and Lambda phage. Furthermore, the most common type of display scaffold relates to the immunoglobulin scaffold with common formats including single chain fragment variable (scFv), domain antibodies (Dab) or Fragment antigen-binding (Fab) format. The scaffold domains can be converted to a display amenable format and cloned into appropriate phage (or phagemid) or yeast vectors where they are genetically fused with a host protein that is located on the surface of the phage (e.g pIII) or yeast (Aga2 fusion) using conventional procedures. There are multiple other scaffolds that are amenable to display including but not limited to peptides, ankyrin repeat proteins, affibodies, anticalins, etc. The variable region of the phage (or an appropriately barcoded region) can be amplified by PCR and sequenced, for example, by next generation sequencing, to determine the variability in clone count of the 'Input' phage library. Oligonucleotide sequencing or alternative methods like mass spectrometry could be used to characterize the library composition.

The constructed library, once displayed on phage, can undergo screening, e.g., bio-panning process. Essentially, the phage library is incubated with a target molecule, e.g., EVs, to which one wishes to isolate specific binders. The EVs can be immobilized on a support, e.g., anti-CD63 magnetic bead. Phage that displays a protein that specifically binds to the support will remain while non-specific binders are washed away. The specific binders are eluted and used to produce more phage, e.g., amplified, via propagation of the phage to produce a phage mixture that is enriched with the relevant binding phage. The enriched library of specific binders can be re-screened against the EVs. The repeated cycling of these steps is referred to as "panning" in reference to enriching a gold sample by removing undesirable material. The phage eluted in the final step can be used to infect a suitable host from which phagemids can be collected and the relevant DNA sequence can be excised and sequenced to identify the relevant protein or protein fragments to aid in profiling EVs from various sources. Using these approaches, phage display libraries that display proteinaceous binding moieties that recognize biomarkers on EVs can obtained and further refined.

Method for Profiling EVs

In one aspect, a method for profiling extracellular vesicles (EV) is provided. The method includes: (a) separately incubating isolated EV from one or more sources with a phage display library under conditions suitable for forming EV-bound phage, wherein the phage display library comprises one or more types of phage, wherein each type of phage having a displayed proteinaceous display binding moieties capable of recognizing one or more epitopes on the surface of the EV, wherein each type of phage comprises nucleic acids encoding the displayed proteinaceous display binding moieties, and wherein the displayed proteinaceous display binding moieties of each type of phage are different; (b) isolating the EV-bound phage; (c) extracting the nucleic acids from the EV-bound phage; (d) amplifying the extracted nucleic acids; (e) sequencing the amplified nucleic acids to identify specific nucleic acid sequences associated with each type of phage from the library that are enriched from the isolated EV; and (f) comparing the specific nucleic acid sequences with nucleic acid sequences from the phage display library and nucleic acid sequences from a control library to identify sequences that can distinguish between EV from the one or more sources.

In one embodiment, the volume of isolated EV and a volume of a phage display library are contacted under any suitable conditions that would allow the EV and phage to form a complex of EV-bound phage. For instance, incubation for 1 to 12 hours, usually 4 hours, at a temperature ranging from 0° C. to 37° C., usually 25° C., allowed for sufficient complex formation. The amount of phage relative to EV can vary, however, a ratio of about 100× phage particles to EV particle can be used. The isolated EV can be obtained from any suitable source and by any suitable isolation procedure as described above. The phage display library can be constructed by any suitable means or can be purchased from commercial sources. A control sample can be prepared by contacting a volume of buffer (instead of isolated EV) with a volume of the phage display library and incubating the mixture under identical conditions.

Thereafter, the EV-bound phage (Output sample) can be separately isolated from the mixture by any suitable procedure. In one embodiment, the output and control samples can be isolated using commercial spin columns such as exoEasy spin columns available from the Qiagen Company, Valencia, Calif. The control sample can be subjected to the same procedure.

In each cycle, the resulting EV-bound phage complexes can be separated from non-binders by any suitable means. Multiple methods exist by which to isolate phage bound specifically to EVs. For instance, EVs may be immunoprecipitated with anti-CD63 beads. Because CD63 is thought to be expressed on a subset of EVs, this method will enrich for a subset of phage that bind to EVs. An alternative example to the bead isolation method, a polymer such as PEG-8000 can be added to the EV phage mixture to a concentration that will precipitate the unbound phage followed by the application of a separation method such as ultracentrifugation to isolate EV-bound phage. For example, at 4% PEG-8000, M13 phage precipitate while EVs do not (Lee et al., 2007; Taylor & Shah, 2015).

DNA from the isolated EV-bound phage (Output sample) can then be extracted by any suitable conventional means including heating at 95° C. for a period of sufficient time to lyse the phage and release the DNA. The extracted DNA is then PCR amplified with suitable primers, and the PCR products can then be purified prior to applying sequencing techniques, e.g., NGS, to identify nucleic sequences that are enriched from each source of isolated EVs by comparing the sequences from Output, Input and Control sample sequences. These unique 'Output' libraries of enriched phage can be compared to the 'Input' library (phage display library) and 'Control' library (no EVs) to determine individual enriched sequences that can distinguish between different sources of EVs. The cognate receptors of individual library elements can be identified using standard affinity pull downs coupled with mass spectrometry. Multiple sequential cycles of library enrichment could be performed to achieve the desired level of enrichment.

A representative method is shown in FIG. 1, in part (A), a single domain antibody "input" phage display library is provided. In FIG. 1, part (B), the input phage display library is then mixed and incubated with isolated EVs from a source, e.g., a subject's plasma. In FIG. 1, part (C), the resulting "output" EV-bound phages can be isolated using bead capture, e.g., anti-CD63 bead capture. A "control" sample involving no EVs is also prepared in parallel to the preparation of the "output" EV-bound complex. In FIG. 1, part (D), alternatively, the "output" EV-bound phages can be isolated by selective polyethylene glycol (PEG) precipitation of unbound phage using varying amounts PEG. The DNA can then be extracted from the "input" phage display library, the "output" EV-bound phage sample, and "Control" sample and the PCR amplified variable regions of the Input, Output and Control can sequenced, e.g., NGS, to determine the enriched sequences of single domain antibodies. See FIG. 1, part (E). The resulting sequencing information allows for the measurement and characterization of molecular biomarkers of EVs from various sources, for the determination of a subject's health and/or disease status, and for the development of therapeutics and diagnostics for diseases.

Example 1

Representative Method for the Preparation of a Phase Display Library

A representative protocol is provided for preparing a glycerol stock of a Domain Antibody (Dab) library and an input phage display library.

1.1 Preparation of the Glycerol Stock of the Domain Antibody (Dab) Library from Supplier Phage Sample 1. Inoculate a single XL1-Blue *E. coli* colony (Agilent Technologies company, Cat. No. 200130) from a fresh plate into 30 mL 2×TY media (Sigma Company, Cat. No. Y2377) in a 125 mL flask. The culture is grown at 37° C. overnight at 250 rpm.
2. Add sufficient volume of the overnight culture to 400 mL 2×TY media into a 2 L vented baffled Erlenmeyer flask to achieve an OD600 of between 0.05 and 0.1.
3. The culture is grown to an OD600 of 0.5 in a shaking incubator at 37° C.
4. 100 uL ($1\times10^{12}$ phage particles) of a Dab library is added to the 400 mL of *E. coli* cells and is incubated without shaking in a 37° C. water bath for 30 minutes. (Total cells=400×8E8×0.5=1.6E11). Note an OD600 of 1.0=$8\times10^{8}$ cells/ml.
5. Carbenicillin and glucose is added to the culture to final concentration of 100 μg/ml carbenicillin and 2% glucose and the resulting culture is incubated at 30° C. for 4 hours at 225 rpm.
6. Centrifuge the culture at 3500 g for 15 min at 20° C.
7. Remove the bacterial supernatant and resuspend the pellet in 10 mL 2×TY media containing 15% glycerol. Divide in 1 mL aliquots, snap freeze in liquid nitrogen and store at −80° C.

1.2 Production of a Large Naive Input Phage Stock of the Human Dab Library from *E. coli* Glycerol Stock as a Library Source 1. Inoculate 1000 mL of 2×TY media containing 2% glucose, 100 ug/ml carbenicillin and 15 ug/ml of tetracycline with 1 mL of the *E. coli* glycerol stock produced in protocol 1.1.7. The OD600 after inoculation should not exceed 0.1.
2. The culture is grown to OD600 of 0.5 in a shaking incubator at 37° C.
3. Infect culture with M13K07 helper phage (Invitrogen, cat. No. 18211-019) at a multiplicity of infection of 20:1 and incubate at 37° C. for 1 hour with no shaking.
4. Centrifuge the culture at 3500 g for 30 min at 20° C.
5. Remove the culture supernatant and re-suspend the pellet in 1000 ml 2×TY media containing, 100 μg/ml carbenicillin, 50 μg/ml kanamycin, and 0.1% glucose and incubate at 25° C. at 250 rpm in a shaking incubator for 20 hours.
6. Centrifuge twice at 4500 g for 30 minutes at 4° C., changing centrifuge bottles in between. Filter supernatant through a 0.44 um low protein binding filter unit. Do not use a 0.22 um filter or filter material that is for general purpose filtration.
7. Add ⅕ volume of 20% PEG6000 containing 2.5M NaCl to the filtered supernatant and incubate for at least 120 minutes at 4° C.
8. Centrifuge precipitated phage for 1 hour at 4° C. at 4500 g. Remove supernatant and re-suspended phage pellets in 50 mL of PBS containing 10% glycerol.
9. Dilute phage pool 1 in 10 in PBS and measure OD270 which came to 0.59. Conversion to phage/mL=estimated according to the following empirical formula: OD270× dilution factor×$1.1\times10^{13}$.
10. Adjust concentration of phage to $1\times10^{13}$ phage/mL with PBS, distribute into 1 mL aliquots, snap freeze in liquid nitrogen and store at −80° C.

Representative Method for EV Isolation

EVs may be isolated from many different sources. If EVs are isolated from tissue culture cells, begin the isolation from protocol 2.1. For plasma, serum, or other bodily fluid, begin at protocol 2.2.

2.1 Production of Conditioned Media from Tissue Culture Cells

1. Seed $6\times10^{6}$ adherent cells in a T150 flask with a total of 20 mL of the appropriate media supplemented with 10% FBS.
2. Grow culture for 48 hours in an incubator with 37° C. with 5% $CO_2$ and 95% relative humidity.
3. Remove the media and wash twice with 20 mL PBS.
4. Add 16 mL of DMEM media supplemented with 10% extracellular vesicle depleted FBS.
5. Grow culture for 48 hours in an incubator with 37° C. with 5% $CO_2$ and 95% relative humidity.
6. Collect the media into a 50 mL Falcon tube.

2.2 Removal of Cells and Cellular Debris

1. Spin samples for 10 min at 4° C. at 500 g in an Eppendorf swinging bucket centrifuge (W30) to remove any intact cells. Carefully remove supernatant without disturbing the pellet and place in new 50 mL Falcon tube on ice.
2. Spin samples for 10 min at 4° C. at 2,000 g in an Eppendorf swinging bucket centrifuge (W30) to remove any cellular debris. Carefully remove supernatant leaving behind the bottom ~0.5 mL and place in new 50 mL Falcon tube on ice.

2.3 Isolation of EVs by Ultracentrifugation

1. Transfer 8 mL of sample to 13.5 mL thick wall ultracentrifuge (UC) tubes. For samples less than 8 mL, add PBS until the total volume is 8 mL. Weigh tubes and equalize the tubes by adding PBS.
2. Spin samples at 100,000 g for 90 minutes at 4° C. in the Optima MAX-XP Ultracentrifuge (W25) using the MLA55 rotor.
3. Pour off supernatant carefully, avoiding disturbing the pellet. Resuspend in cold PBS. Spin samples at 100,000 g for 90 minutes at 4° C. in the Optima MAX-XP Ultracentrifuge (W25) using the MLA55 rotor. Repeat this step, for a total of 2 washes in PBS.
4. Re-suspend the pellet in 200 uL of PBS. To determine the concentration of EVs, dilute 10 uL of sample into 990 uL PBS, and measure on the Nanosight LM-10.
5. Adjust EV concentration by adding PBS to a final concentration of $1\times10^{11}$ EVs/mL.

Representative Method for EV-Bound Phase Complex Formation and Isolation

A representative protocol for the formation of EV-phage complex formation and isolation is provided below.

3. Incubation of EVs and Phage—Input, Control, and Output Samples

1. For the 'Input' sample, add 100 uL of the human Dab library ($1\times10^{13}$ phage/mL) to 300 uL of elution buffer XE, place on ice and do not use this sample until step 1. of the 5.1 NGS section.
2. For the 'Output' sample, add 100 uL of the EV sample ($1\times10^{11}$ EVs/mL) to 100 uL of the phage library ($1\times10^{13}$ phage/mL) to 200 uL of binding buffer XBP and incubate at room temperature for 4 hours. This gives a total of $10^{10}$ EVs incubated with a total of $10^{12}$ phage.

3. As the 'Control' sample, add 100 uL of PBS to 100 uL of the phage library ($1\times10^{13}$ phage/mL) to 200 uL of binding buffer XBP and incubate at room temperature for 4 hours.

4. Phage-EV Complex Isolation—Control and Output Samples

1. Add the total 400 uL of the Control and Output samples to the exoEasy spin column and centrifuge for 1 minute at room temperature at 500 g in an eppendorf swinging bucket centrifuge (W30). Discard the flow through.

2. Add 10 mL of wash buffer XWP to each exoEasy spin column and centrifuge for 5 minutes at room temperature at 3,000 g in an eppendorf swinging bucket centrifuge (W30). Discard the flow through.

3. Transfer each exoEasy column to a new collection tube and add 400 uL of elution buffer XE to the column and incubate for 5 minutes. Centrifuge for 5 minutes at room temperature at 500 g in an eppendorf swinging bucket centrifuge (W30). Collect the elution which should be about 400 uL. Store on ice.

Representative Method for DNA Extraction from EV-Bound Phage and DNA Sequencing

Protocols for the extraction of DNA from the isolated EV-bound phage and subsequent DNA sequencing provided below.

5. Next Generation Oligonucleotide Sequencing (NGS)

1. Heat the Input sample, and the Control and Output elutions to 95° C. for 10 minutes to lyse the phage.

2. PCR amplify the lysed phage of each using NEB's hot start Q5 polymerase using the manufacturer's instructions with the following primers:

```
                                        (SEQ ID NO: 01)
Forward: AATGATACGGCGACCACCGAGATCTACACGGG
GGAGGCTTGGTACAGCCT (SEQ ID NO: 02)
Reverse: CAAGCAGAAGACGGCATACGAGATAGACGGTG
ACCAGGGTTCCCTGA
```

3. Purify the PCR product with AmpureXP® beads (Beckman Coulter company, Cat. No. A63880).

4. Sequence the material using a 150 paired end base pair cycle on an Illumina HiSeq 4000® machine using the Illumina HiSeq 3000/4000 PE Clusters Kit (Illumina company, Cat. No. PE-410-1001) and HiSeq 3000/4000 SBS® Kit (Illumina company, Cat. No. FC-410-1001).

5. For each Dab phage sequence in the Input sample, generate a null distribution based on the number of reads for the same sequence in the Control sample. The null distribution represents the expected distribution of counts due to nonspecific binding of each phage to the exoEasy® column. Then, the number of reads for each sequence in the Output sample can be compared against this expectation, and a significance value (p-value) can be attached to the difference, corresponding to the degree of enrichment of each phage sequence.

6. Compare the entire set of p-values generated from different sources to determine individual sequences that can distinguish between them.

Example 2

Capture of Anti-Her2 Phage Particles on EVs Captured on Anti-HER2 Magnetic Beads In this Example, two types (MDA MB 231 and Au565) of EVs isolated from human MDA MB 231 and Au565 cells (from ATCC) using the isolation procedure is produced using the following method. EVs were purified from 80 mL of conditioned media collected from a confluent 5 layers multi flask of AU565 (Her2 positive cells) and MDAMB231 (Her2 negative cells)). 16 mL of conditioned media were loaded on one ExoEasy column and the eluted fractions from 5 columns were combined. The EV elution buffer was exchanged to PBS with NAP5 (GE) columns. The EVs preparation was loaded on a Amicon® Ultra-4 Centrifugal Filter Unit (molecular weight cut-offs 30 kDa, EMD millipore) and concentrated by centrifugation to 150 microL. EVs concentration was assessed by Nanosight LM10 (Malvern Instruments) as 1.35E+10 EV/mL from MDAMB231 and 1.03E+10 EV/mL from Au565.

The purified EVs were then captured on anti-HER2 magnetic beads as follows. The purified EV (2, 6, 12, 100 microL) were incubated for 2 hours at room temperature on a rotating platform with 10 uL of Goat anti-mouse IgG Dynabeads (Thermo Fisher), previously coated anti-Her2 (24D2, Biolegend) antibody as recommended by manufacturer, or no beads control in PBS with 0.1% BSA. After incubation, the EV-captured anti-HER2 magnetic beads were magnetically captured and washed 3 times in PBS with 0.1% BSA.

Anti-HER2 magnetic bead-EV-phage complexes are generated as follows. The EV-captured anti-HER2 magnetic beads were resuspended in 100 microL of PBS with 0.1% BSA and incubated with 1.5E+10 M13 phage bearing the anti-HER2 nanobody, 5F7 (ref. Pruszynski M, Koumarianou E, Vaidyanathan G, Revets H, Devoogdt N, Lahoutte T, Zalutsky M R. Nucl Med Biol. 2013 January; 40(1):52-9 PMID: 23159171), for 1 hour rotating at room temperature. After incubation beads are magnetically captured and washed 3 times in PBS with 0.1% BSA and resuspended in 100 microL of PBS with 0.1% BSA.

Thereafter, 10 uL of beads slurry or no beads control was diluted into 990 uL PBS and 2 microL were taken and added to 18 uL of qPCR master mix (PowerUp SYBR Green Master Mix from Thermo Fisher, with 10 µM forward primer

```
(5'-CACTCATTAGGCACCCCAG; SEQ ID NO: 03)
``` and 10 µM reverse primer

```
(5'-GTTATCCGCTCACAATTCCAC; SEQ ID NO: 04)).
```

Samples were subjected to PCR reaction in a Thermocycler and threshold cycle number (CT) were collected. A set of calibration standards of known amount of M13 phage was employed to generate a standard curve that was used to convert threshold cycle number (CT) to number of phage bound to EV captured on magnetic beads. The results are shown in FIG. 2.

Figure 2:
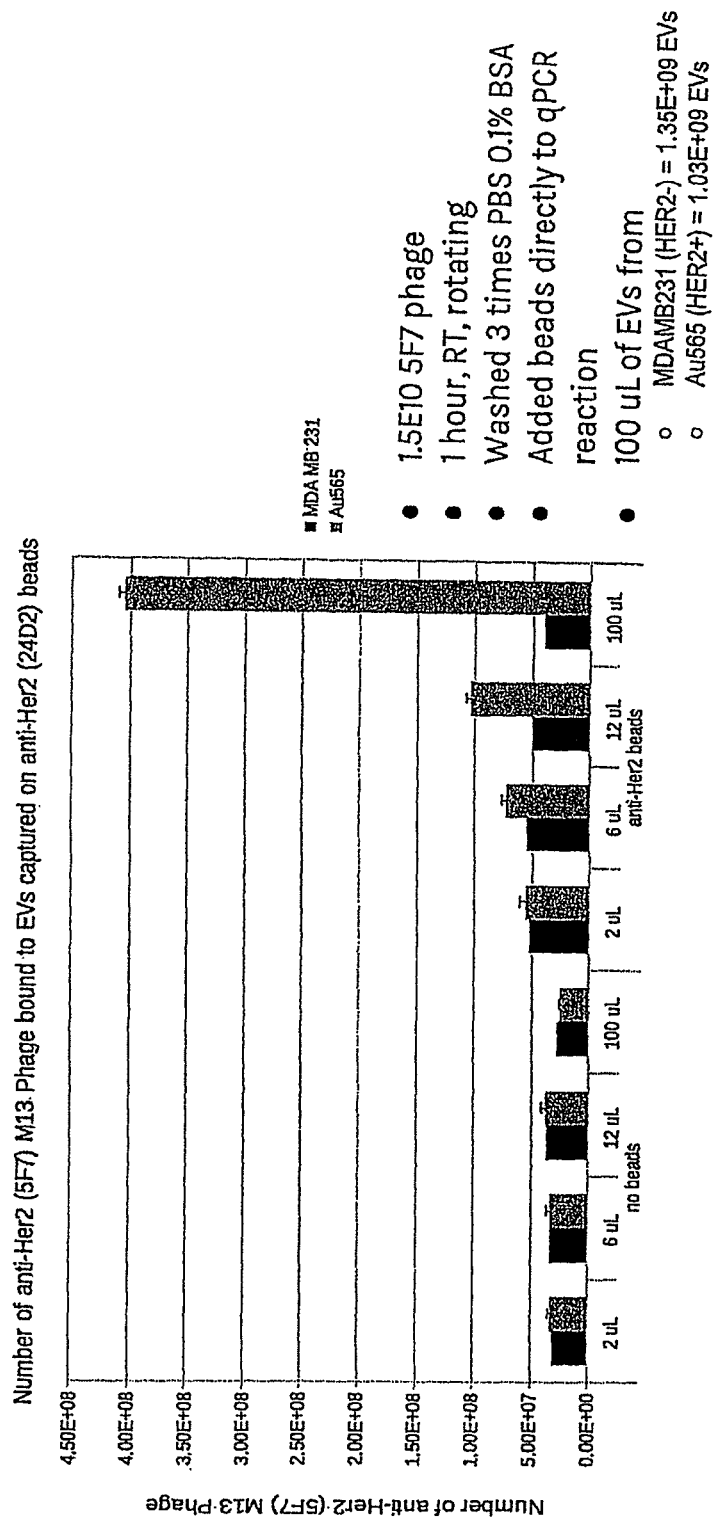
FIG. 2 is a graph showing the successful capture of anti-HER2 phage particles on EVs captured on anti-HER2 magnetic beads. The Y axis shows the number of anti-HER2 (5F7) M13 phage particles bound to EVs (MDA MB 231 or Au565) captured on anti-HER2 (24D2) beads. The controls had no beads.

As shown in FIG. 2, the number of anti-HER2 (5F7) M13 phage bound to EVs captured on anti-HER2 beads had increased for 2 uL, 6 uL, 12 uL, and 100 uL aliquots where Au565 EVs were used. In contrast, no parallel increases were seen for 2 uL, 6 uL, 12 uL and 100 uL of MDA MB 231 EVsS.

Various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A method for profiling extracellular vesicles (EVs), the method comprising:
   incubating isolated EVs from one or more sources with a phage display library under conditions suitable for forming EV-bound phage complexes, wherein the phage display library comprises one or more types of phage, each type of phage having a displayed Dab, Fab, or scFv capable of binding one or more epitopes on the surface of the EVs, wherein each type of phage comprises nucleic acids encoding the displayed Dab, Fab, or scFv, and wherein the displayed Dab, Fab, or scFv of each type of phage is different;
   isolating the EV-bound phage complexes;
   extracting the nucleic acids from the EV-bound phages;
   amplifying the extracted nucleic acids;
   sequencing the amplified nucleic acids to identify specific nucleic acid sequences from the EV-bound phages; and
   identifying the epitopes present on the surface of the EVs of the EV-bound phage complexes.

2. The method according to claim 1, wherein the isolated EVs are obtained from a bodily fluid.

3. The method according to claim 1, wherein the isolated EVs are obtained from cell lines, serum, plasma, urine, saliva, or cerebral fluid.

4. The method according to claim 1, wherein the EV-bound phage complexes are isolated by immunoprecipitation.

5. The method according to claim 1, wherein the EV-bound phage complexes are isolated by polymer precipitation.

6. The method according to claim 1, wherein the EVs are isolated by immunoprecipitation, ultracentrifugation, or affinity purification.

7. The method according to claim 1, wherein M13 phage is used to generate the phage display library.

* * * * *